United States Patent [19]

Omura et al.

[11] Patent Number: 4,892,821
[45] Date of Patent: Jan. 9, 1990

[54] METHOD FOR PREPARING VITAMIN D COMPOUNDS

[75] Inventors: Sadafumi Omura, Ageo; Joji Sasaki, Omiya; Akiko Mikami; Kazutoshi Mizoue, both of Urawa, all of Japan

[73] Assignee: Taisho Pharmaceutical Co., Ltd., Japan

[21] Appl. No.: 215,316

[22] Filed: Jul. 5, 1988

[30] Foreign Application Priority Data

Jul. 8, 1987 [JP] Japan ............................... 62-170669
Dec. 26, 1987 [JP] Japan ............................... 62-331323

[51] Int. Cl.$^4$ ...................... C12P 15/00; A61K 31/59; C12R 1/04; C12R 1/465
[52] U.S. Cl. .................................. 435/127; 260/397.2; 435/155; 435/157; 435/158; 435/826; 435/872; 435/886; 514/167
[58] Field of Search ............... 435/155, 127, 157, 158, 435/826, 886, 872; 260/397.2; 514/167

[56] References Cited

U.S. PATENT DOCUMENTS

| 4,279,826 | 7/1981 | DeLuca et al. | 260/397.2 |
| 4,284,577 | 8/1981 | Yamada et al. | 260/397.2 |
| 4,338,250 | 7/1982 | DeLuca et al. | 260/397.2 |
| 4,502,991 | 3/1985 | DeLuca et al. | 260/397.2 |
| 4,689,180 | 8/1987 | DeLuca et al. | 260/397.2 |
| 4,711,881 | 12/1987 | Ikekawa | 260/397.2 |
| 4,717,721 | 1/1988 | DeLuca et al. | 260/397.2 |
| 4,719,205 | 1/1988 | DeLuca et al. | 260/397.2 |

*Primary Examiner*—Herbert J. Lilling
*Attorney, Agent, or Firm*—Lorusso & Loud

[57] ABSTRACT

A method for introducing hydroxyl groups into vitamin D compounds at 1α- and/or 25-positions by use of a solution containing the mycelium of Actinomycetales being capable of hydroxylating vitamin D compound or the enzyme produced from the mycelium, is disclosed.

10 Claims, No Drawings

METHOD FOR PREPARING VITAMIN D COMPOUNDS

BACKGROUND OF THE INVENTION

1. Field of the Invention

The present invention relates to a method for preparing hydroxyvitamin D compounds using microorganisms.

2. Description of the Prior Art

It is very difficult to directly introduce hydroxyl groups into vitamin D compounds at the 1α- and/or 25-positions by the method of organic synthesis, and such introduction has not yet been reported.

Furthermore, any methods of enzymatic chemistry for introducing directly hydroxyl group into vitamin D compounds using microorganism have not yet been reported, either.

It was possible in the past to directly introduce hydroxyl groups into vitamin D compounds at the 1α- and/or 25-positions by the method of enzymatic chemistry using animal organs. Namely, there were known the methods for introducing directly a hydroxyl group at the 1α-position using the homogenate or mitochondoria fractions of kidney of animals such as chicken [Nature, vol. 230, p. 228 (1971), J. Biolog. Chem. vol. 247, p. 7528 (1972), and Biochemistry, vol. 25, p. 5512 (1986)]. In addition, there were known the methods for introducing directly a hydroxyl group at the 25-position by perfusing a solution containing vitamin D compound with liver collected from animals such as rats [J. Clin. Invest., vol. 48, p. 2032 (1969), and Biochem. Biophys. Res. Commun., vol. 66, p. 632 (1975)] or using the homogenate of liver of animals such as rats [Biochem. Biophys. Res. Commun., vol. 36, p. 251 (1969)].

However, the methods of enzymatic chemistry using animal organs require a large amount of kidney or liver tissue, and the preparation of such organs is very time-consuming. Accordingly, these methods are ineffective and unpractical.

SUMMARY OF THE INVENTION

The present inventors have found how to introduce hydroxyl groups into the vitamin D compounds at 1α- and/or 25-positions using specific microorganisms.

DETAILED DESCRIPTION OF THE INVENTION

An object of the present invention is to provide a method for preparing a 1α- or 25-hydroxyvitamin D compound which comprises adding a vitamin D compound having a hydrogen atom at the 1α- or 25-position to a reaction mixture containing a mycelium of Actinomycetales being capable of hydroxylating vitamin D compound or a reaction mixture containing the enzyme produced from the mycelium and converting the hydrogen atom into a hydroxyl group.

Another object of the present invention is to provide a method for preparing a 25-hydroxyvitamin D compound or 1α, 25-dihydroxy vitamin D compound which comprises adding a vitamin D compound having hydrogen atoms at the 1α- and 25-positions to a reaction mixture containing a mycelium of Actinomycetales being capable of hydroxylating the vitamin D compound or to a reaction mixture containing the enzyme produced from the mycelium and converting the hydrogen atoms into hydroxyl groups.

Still another object of the present invention will become apparent from the following description.

In carrying out the present invention using the vitamin D compounds having a hydrogen atom at the 1α or 25-position, the hydrogen atom can be converted into a hydroxyl group. In case where the vitamin D compounds having hydrogen atoms at the 1α- and 25-positions are used, first the hydrogen atom at the 25-position can be converted into a hydroxyl group, then the hydrogen atom at the 1α-position can be converted into a hydroxyl group.

The present invention is a method by which hydroxyl groups can be introduced into the vitamin D compound at the 1α- and/or 25-positions directly in one step, and the vitamin D compound may have any substitutents at any positions other than the 1α- or 25-position. Accordingly, the vitamin D compounds used in the present invention include the vitamin $D_2$ series and vitamin $D_3$ series wherein the hydrogen atom or hydroxyl group at the 17-position side chain may be substituted by a halogen atom (e.g., a fluorine atom), a hydroxyl group, a lower alkyl group and the like. When the starting vitamin D compound has a substituent other than a hydrogen atom at the 1α- or 25-position, one of the preferred substituents is a hydroxyl group. Examples of the vitamin D compounds are vitamin $D_2$, vitamin $D_3$, 1α-hydroxyvitamin $D_3$, 1α, 24-dihydroxyvitamin $D_3$, 25-hydroxyvitamin $D_3$, 25-hydroxyvitamin $D_2$, 24, 25-dihydroxyvitamin $D_3$, 23, 25-dihydroxy-vitamin $D_3$, 25, 26-dihydroxyvitamin $D_3$, 23, 24, 25-trihydroxyvitamin $D_3$, 24, 24-difluoro-25-hydroxy-26, 27-dimethylvitamin $D_3$, 25-hydroxy-26, 26, 26, 27, 27, 27-hexafluorovitamin $D_3$ and the like.

The Actinomycetales used in the present invention are those being capable of introducing hydroxyl groups into vitamin D compounds at the 1α- and/or 25-positions such as, for example, genus Actinomadura, genus Rhodococcus, genus Chainia, genus Streptoverticillium, genus Actinomyces, genus Actinoplanes, genus Micromonospora, genus Nocardia and genus Streptomyces. Preferred are (1) the strain which was newly isolated from a soil sample collected by the present inventors at Omiya-city, Saitama prefecture, Japan, and which has been deposited with Fermentation Research Institute, the Agency of Industrial Science and Technology under the name of "*Streptomyces sclerotialus* T-JS1" with Deposition Number FERM BP-1370,, (2) the strain which was newly isolated from a soil sample collected by the present inventors at Torisawa-mura, Minamitsuru-gun, Yamanashi Prefecture, Japan, and which has been deposited with Fermentation Research Institute, the Agency of Industrial Science and Technology under the name of "*Streptomyces roseosporus* A-5797" with Deposition Number FERM BP-1574, and (3) the strain which was newly isolated from a soil sample collected by the present inventors at Omiya-city, Saitama Prefecture, Japan, and has been deposited with Fermentation Research Institute, the Agency of Industrial Science and Technology under the name of "*Nocardia autotrophica* N-102" with Deposition Number FERM BP-1573.

The morphological properties of these strains are as follows.

a. *Streptomyces sclerotialus* T-JS1

(1) Morphology

Vegetative mycelium can grow well on synthetic agar media and natural agar media with branching. Aerial mycelium is poorly developed on yeast-malt extract agar, oatmeal agar, inorganic salts-starch agar and glycerol-asparagine agar. The aerial mycelium branches monopodially with spiral spore chains. Usually, the spore chains have ten or more spores with smooth surfaces. The spore is cylindrical in shape and $0.57-1.0 \times 0.64-1.4$ μm in size. The spiral spore chains grow on inorganic salts-starch agar medium abandantly. Sclerotia in the vegetative mycelium is observed. When cultivation is carried out on yeast-malt extract agar medium for 2 weeks, the coalesced masses of spores having the morphology similar to that of sporangia are observed. Flagellated spore is not observed.

(2) Growth on media

The cultivation was carried out on various media at 28° C. for 14 days, and the results of the macroscopic observation are shown in Table 1.

TABLE 1

| Medium | Growth on Medium | Color of Reverse Side of Colonies | Aerial mycelium Formation | Aerial mycelium Color | Soluble Pigment |
|---|---|---|---|---|---|
| Sucrose-nitrate agar | moderate pale yellow elevated | pale brown | poor | — | none |
| Glucose-asparagine agar | moderate creamy moist | pale brown | slightly formed | creamy | none |
| Glycerol asparagine agar | moderate creamy moist wrinkle | pale brown | poor | — | none |
| Inorganic salts-starch agar | good creamy elevated | creamy | slightly formed | white | none |
| Tyrosine agar | moderate creamy elevated | creamy | slightly formed | creamy | none |
| Nutrient agar | moderate creamy moist wrinkle | creamy | poor | — | none |
| Yeast-malt extract agar | moderate creamy moist | yellow-ish brown | slightly formed | creamy | none |
| Oatmeal agar | moderate creamy moist | pale brown | slightly formed | creamy | none |
| Peptone-yeast-iron agar | moderate pale yellow moist wrinkle | pale brown | poor | — | none |

(3) Physiological properties

(1) Temperature range for Growth

The optimum temperature for growth is between 25° C. and 37° C. on inorganic salts-starch agar.

There is no growth at 10° C. or below, or at 45° C. or above.

(2) Biochemical Properties (a) Distinction between aerobic and anaerobic: aerobic
(b) Liquefaction of gelatin: positive
(c) Coagulation of skim milk: negative
(d) Peptonization of skim milk: positive
(e) Hydrolysis of starch: positive
(f) Formation of melanin-like pigment: negative

(3) Utilization of carbon sources (Pridham/Godlieb agar medium)

All of the following carbon sources are utilized. D-glucose, D-fructose, inositol, galactose, starch, sucrose, rhamnose, D-mannitol, L-arabinose, D-xylose, raffinose.

It is apparent from the above properties that this strain belongs to Actinomycetales. These properties were compared with those of strains reported in I.S.P., The International Streptomyces Project; Bergey's Manual of Determinative Bacteriology, 8th edition (1974); and Waxman's, The Actinomycetes, vol. 2 (1961), and this strain was found to be most similar to *Streptomyces sclerotialus*.

As a result of the above, this strain is concluded to be the same species as *Streptomyces sclerotialus* and named *Streptmyces sclerotialus* T-JS1.

b. *Streptomyces roseosporus* A-5797

(1) Morphology

Vegetative mycelium grows well on synthetic agar media and natural agar media with irregular branching. No septum is observed. Spore chains are formed abandantly on grycerol-asparagine agar, inorganic salts-starch agar, oatmeal agar and the like. By microscopic observation, the aerial mycelium branches monopodially with straight spore chains. The spore chains have ten or more spores, and the long spore chains are developed at the stationary phase of the culture. The spore is smooth surfaced, oval in shape and $0.67-0.75$ μm $\times 1.30-1.58$ μm in size. Sclerotia, sporangia and flagellated spores are not observed

(2) Growth on media

The cultivation was carried out on various media at 30° C. for 14 days, and the results of the macroscopic observation are shown in Table 2.

TABLE 2

| Medium | Growth on Medium | Color of Reverse Side of Colonies | Aerial mycelium Formation | Aerial mycelium Color | Soluble Pigment |
|---|---|---|---|---|---|
| Sucrose-nitrate agar | moderate | creamy | slightly poor | creamy | none |
| Glucose-asparagine agar | moderate | creamy | slightly poor | creamy | none |
| Glycerol asparagine agar | good | pale yellow | good | light grayish red | none |
| Inorganic salt-starch agar | good | pale yellow | good | light grayish red | none |
| Tyrosine agar | good | pale yellow | good | light grayish red | none |
| Nutrient agar | moderate | creamy | none | — | none |
| Yeast-malt extract agar | good | pale yellow | good | light grayish red | none |
| Oatmeal agar | good | creamy | good | light grayish red | none |
| Peptone-yeast-iron | good | pale brown | none | — | none |

TABLE 2-continued

| Medium | Growth on Medium | Color of Reverse Side of Colonies | Aerial mycelium Formation | Aerial mycelium Color | Soluble Pigment |
|---|---|---|---|---|---|
| agar | | | | | |

(3) Physiological properties (1) Temperature range for Growth

The optimum temperature for growth is between 20° C. and 30° C. on oatmeal agar.

There is no growth at 10° C. or below, or at 40° C. or above.

(2) Biochemical Properties (a) Distinction between aerobic and anaerobic: aerobic
(b) Liquefaction of gelatin: positive
(c) Coagulation of skim milk: negative
(d) Peptonization of skim milk: positive
(e) Hydrolysis of starch: positive
(f) Formation of melanin-like pigment: negative
(g) Cell wall type: I (3) Utilization of carbon sources Pridham/Godlieb agar medium)

Utilizable: D-glucose, L-arabinose, D-xylose, Slightly utilizable: D-fructose, rhamnose, Not utilizable sucrose, inositol, raffinose, D-mannitol.

It is apparent from the above properties that this strain belongs to Actinomycetales. These properties were compared with those of strains reported in I.S.P., The International Streptomyces Project; Bergey's Manual of Determinative Bacteriology, 8th edition (1974); and Waxman's, The Actinomycetes, vol. 2 (1961), and this strain was found to be most similar to *Streptomyces roseosporus*.

As a result of the above, this strain is concluded to be the same species as *Streptomyces roseosporus* and named as *Streptmyces roseosporus* A-5797.

c. *Nocardia autotrophica* N-102

Vegetative mycelium grows well on synthetic agar media and natural agar media with irregular branching. No septum is observed. Spore chains are formed abundantly on glycerol-asparagine agar, inorganic salts-starch agar and the like. By microscopic observations, the aerial mycelium branches monopodially with straight spore chains The spore chains have 3 or more spores, and the long spore chains are developed at the stationary phase of the culture. The spore is smooth surfaced, cylindrical in shape and 0.5–0.8 $\mu m \times 2.5$–4.3 $\mu m$ in size. Sclerotia, sporangia and flagellated spores are not observed.

(2) Growth on media

The cultivation was carried out on various media at 30° C. for 14 days, and the results of the macroscopic observation are shown in Table 3.

TABLE 3

| Medium | Growth on Medium | Color of Reverse Side of Colonies | Aerial mycelium Formation | Aerial mycelium Color | Soluble Pigment |
|---|---|---|---|---|---|
| Sucrose-nitrate agar | moderate | pale brown | moderate | creamy | none |
| Glucose-asparagine agar | slightly poor | creamy | moderate | white | none |
| Glycerol-asparagine agar | good | pale yellow | good | white | none |
| Inorganic salt-starch agar | moderate | creamy | good | white | none |
| Tyrosine agar | moderate | reddish brown | good | creamy | pale reddish brown |
| Nutrient agar | good | pale yellow | good | white | none |
| Yeast-malt extract agar | good | pale yellow | slightly poor | white | none |
| Oatmeal agar | moderate | creamy | slightly poor | white | none |
| Peptone-yeast-iron agar | moderate | pale brown | moderate | creamy | none |

(3) Physiological properties (1) Temperature range for Growth

The optimum temperature for growth is between 20° C. and 30° C. on nutrient agar.

There is no growth at 10° C. or below, or at 45° C. or above.

(2) Biochemical Properties (a) Distinction between aerobic and anaerobic: aerobic
(b) Liquefaction of gelatin: negative
(c) Coagulation of skim milk: negative
(d) Peptonization of skim milk: negative
(e) Hydrolysis of starch: negative
(f) Formation of melanin-like pigment: negative
(g) Nitrate reduction: negative (3) Utilization of carbon sources Pridham/Godlieb agar medium)

Utilizable: D-glucose, L-arabinose, sucrose, D-xylose, L-inositol, D-mannitol, D-fructose, rhamnose
Slightly utilizable: raffinose It is apparent from the above properties that this strain belongs to Actinomycetales. These properties were compared with those of strains reported in I.S.P., The International Streptomyces Project; Bergey's Manual of Determinative Bacteriology, 8th edition (1974); and Waxman's, The Actinomycetes, vol. 2 (1961), and this strain was found to be most similar to *Nocardia autotrophica*.

As a result of the above, this strain is concluded to be the same species as *Nocardia autotrophica* and named *Nocardia autotrophica* N-102.

The present invention can be carried out by the reaction of the substrate vitamin D compound in a solution containing the mycelium of the strain belonging to the Actinomycetales or a solution containing the enzyme prepared from the mycelium under the arerobic conditions.

In order to obtain the mycelium of the Actinomycetales necessary for the reaction, cultivation can be carried out in a medium under the aerobic conditions.

A liquid medium is chiefly used. The carbon sources used for the medium are glucose, maltose, dextrose, starch, arabinose and xylose, and they are used alone or in admixture. The nitrogen sources used are polypeptone, casamino acid, yeast extract, meat extract, corn steep liquor, soybean meal and the like, and they are used alone or in admixture. Furthermore, if necessary, organic substances or inorganic salts can be used in order to aid the growth of the strain and to promote the transformation of vitamin D compound having hydroxyl groups at $1\alpha$- and/or 25-positions. Preferred cultivations of the strain are performed in aerobic conditions such as shaking culture at pH 6 to 7.4 at 28° to 30° C. for 2 to 8 days.

According to the method of the present invention, the reaction mixture containing the mycelium may be used. Namely, the culture medium is continuously adopted for the reaction mixture. Alternatively, after completion of the cultivation, the mycelium obtained by cultivation is separated by centrifugation or filtration and suspended in a buffer solution in order to be adopted for the reaction mixture. In addition, the supernatant containing the enzyme obtained by sonicating the mycelium is also adopted for the reaction mixture. Preferably, centrifugation is carried out after the sonication in order to obtain the supernatant. The mycelium can be also added to a solution after fixing with optically cross-linking resin prepolymers such as ENT 3400 (trade name, Kansai Paint Co.), urethane prepolymers such as PU-9 (trade name, Toyo Gum Co.) and polysaccharide such as $\kappa$-caraginane. Furthermore, the lyophillized mycelium may be used for the same method as described above.

Examples of the solution adopted for the reaction mixture in the present invention are the media as described above as well as buffer solutions such as tris-acetate, tris-hydrochloride, sodium succinate-succinic acid, potassium succinate-succinic acid, sodium citrate-citric acid, sodium phosphate, potassium phosphate, sodium phosphate-potassium phosphate, sodium cacodylate-hydrochloric acid, imidazole-hydrochloric acid, sodium borate-boric acid and like, and they are used alone or in admixture. If necessary, detergents, organic substances and inorganc salts can be added to the reaction mixture in order to aid the growth of the strain and to promote the transformation of vitamin D compound.

According to the method of the present invention, in case where the reaction mixture containing the above mycelium or enzyme is used, this reaction mixture is preferably shaken or stirred at pH 5 to 8, at 20° to 37° C. for 5 minutes to 96 hours under aerobic conditions. These procedures can be also carried out under an oxygen atmosphere. The suitable amount of the substrate vitamin D compound can be added at the begining of reaction.

In case where the reaction mixture containing the mycelium in culture medium is used, the substrate is added and then the cultivation is continued for an additional 24 to 96 hours under the same conditions as described above.

In case where the vitamin D compounds having hydrogen atoms at $1\alpha$- and 25-positions is used as a substrate, the reaction time can be determined by confirming the product by use of high performance liquid chromatography as described below so as to give the final 25-hydroxyvitamin D compound or $1\alpha$, 25-dihydroxyvitamin D compound.

Isolation of the vitamin D compound thus obtained can be accomplished by the ordinary method by which the vitamin D is collected and isolated from blood. For example, after completion of the reaction, the reaction mixture is extracted with an organic solution and concentrated to dryness. This is dissolved in a suitable solvent such as 2-propanol-n-hexane, centrifuged to remove the insolubles, and applied to a high performance liquid chromatograph using silica gel normal phase column (e.g., Zorbax SIL, column size 4.6 mm $\phi \times 25$ cm, Du Pont Co., U.S.A.) or silica gel reverse phase column (e.g., Zorbax ODS, column size 4.6 mm $\phi \times 25$ cm, Du Pont Co., U.S.A.) to isolate the final hydroxy vitamin D compound.

The present invention makes it possible to indroduce hydroxyl groups directly into vitamin D compounds at the $1\alpha$- and/or 25-positions. Namely, in the method using the microorganism of the present invention, it is not time-consuming to prepare the microorganism and the reaction mixture, and the introduction of hydroxyl groups can be carried out extremely easily and effectively for a short time in one step.

The present invention will be illustrated in more detail by the following Examples and Experiment.

EXAMPLE 1

Fifty ml of a sterile liquid medium (pH 7.0) containing 1% of starch, 1% of maltose, 1% of dextrin, 1.5% of soybean meal, 0.3% of meat extract, 0.5% of casamino acid and 0.4% of calcium carbonate, in each of five 500 ml Erlenmeyer flasks, was inoculated with one platinum loop of *Streptomyces sclerotialus* T-JS1, and shaking culture was carried out at 30° C. for 48 hours. After completion of the cultivation, the culture medium was centrifuged to collect the mycelium, which was then suspended in 200 ml of a buffer solution (pH 7.4) containing 15 mM tris-acetate, 25 mM sodium succinate, 2 mM magnesium acetate and 200 mM sucrose (hereinafter referred to as "Buffer solution A"). This suspension was again centrifuged to collect the mycelium, which was then suspended in 200 ml of Buffer solution A with thorough stirring. Forty ml of the suspension was placed in each of five 500 ml Erlenmeyer flasks and kept warm at 30° C. for 5 minutes. A solution of 400 $\mu$g of the substrate 25-hydroxyvitamin $D_3$ in 400 $\mu$l of ethanol was added to each of the five Erlenmeyer flasks, and reaction processed at 30° C. for 45 minutes with shaking. The reaction mixtures in the Erlenmeyer flasks were combined, and extracted with 1 l of methylene chloride. The methylene chloride layer was concentrated to dryness at 40° C. or below under reduced pressure, immediately dissolved in 7.5 ml of a mixture of 2-propanol and n-hexane (1:9) and allowed to stand at $-20°$ C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm $\phi \times 25$ cm, Du Pont Co., U.S.A.) under the following conditions.

Eluent: 2-propanol:n-hexane=1:9
Column temperature: 25° C.
Elution rate: 1.5 ml/minute
Detection: Use of Photodiode array detector (MCPD 3500, Otsuka Electric Co.)

After elution, the peak fractions having a retention time of about 15.4 minutes and the same UV absorption pattern as those of the vitamin D compounds were collected, concentrated at 40° C. or below under reduced pressure and applied to a high performance liquid chromatograph (Zorobax ODS, column size 4.6 mm $\phi \times 25$ cm, Du Pont Co., U.S.A.) under the following conditions.

Eluent: water:methanol = 1:9
Column temperature: 40° C.
Elution rate: 1.0 ml/minute
Detection: Use of Photodiode array detector (MCPD 3500, Otsuka Electric Co.)

After elution, the peak fractions having a retention time of about 5.6 minutes and the same UV absorption pattern as those of the vitamin D compounds were collected, and concentrated to dryness at 40° C. or below under reduced pressure with a nitrogen gas replacement to give 200 µg of 1α, 25-dihydroxyvitamin $D_3$, which was identical to the authentic sample of the commercially available 1 , 25-dihydroxyvitamin $D_3$ (Duphar Co., Netherland) in terms of the retention time of a high performance liquid chromatograph (Zorbax SIL, column size 4.6 mm $\phi \times 25$ cm), the UV absorption spectrum, mass spectrum cleavage pattern.

Maximum UV Absorption: $\lambda_{max} = 265$ nm (ethanol).
EI-MS (m/z): 416($M^+$), 398($M^+$-$H_2O$), 380($M^+$-$2H_2O$), 287, 269, 258, 251, 152, 134, 129, 116, 111, 59.

EXAMPLE 2

Following a procedure similar to that of Example 1, 1α, 24, 25-trihydroxyvitamin $D_3$ was obtained from 24, 25-dihydroxyvitamin $D_3$.

This compound had a retention time of 29.4 minutes in the high performance liquid chromatograph (Zorbax SIL, column size 4.6 mm $\phi \times 25$ cm) under the same conditions as those of Example 1.

Maximum UV Absorption: $\lambda_{max} = 265$ nm (ethanol).
EI-MS (m/z): 432($M^+$), 414($M^+$-$H_2O$), 396($M^+$-$2H_2O$), 287, 269, 251, 152, 134, 116, 59.

EXAMPLE 3

Following a procedure similar to that of Example 1, 1α, 25-dihydroxyvitamin $D_2$ was obtained from 25-hydroxyvitamin $D_2$.

This compound had a retention time of 14.4 minutes in the high performance liquid chromatograph (Zorbax SIL, column size 4.6 mm $\phi \times 25$ cm) under the same conditions as those of Example 1.

Maximum UV Absorption: $\lambda_{max}$265 nm (ethanol).
EI-MS (m/z): 428($M^+$), 410($M^+$-$H_2O$), 392($M^+$-$2H_2O$), 287, 269, 251, 152, 134, 116, 59.

EXAMPLE 4

Following a procedure similar to that of Example 1, 1α, 25-dihydroxy-24, 24-difluoro-26,27-dimethylvitamin $D_3$ was obtained from 24, 24-difluoro-25-hydroxy-26,27-dimethylvitamin $D_3$.

Maximum UV Absorption: $\lambda_{max} = 265$ nm (ethanol).
EI-MS (m/z): 480($M^+$), 287, 269, 251, 152, 134, 116.

EXAMPLE 5

Following a procedure similar to that of Example 1, 1α, 25-dihydroxy-26, 26, 26, 27, 27, 27-hexafluorovitamin $D_3$ was obtained from 25-hydroxy-26, 26, 26, 27, 27, 27-hexafluorovitamin $D_3$.

Maximum UV Absorption: $\lambda_{max} = 265$ nm (ethanol).
EI-MS (m/z): 524($M^+$), 287, 269, 251, 152, 134, 116.

EXAMPLE 6

Fifty ml of a sterile liquid medium (pH 7.0) containing 1.5% of glucose, 1.5% of soybean meal, 0.5% of corn steep liquor, 0.5% of sodium chloride and 0.2% of calcium carbonate, in each of five 500 ml Erlenmeyer flasks, was inoculated with one platinum loop of *Streptomyces roseosporus* A-5797 and shaking culture was carried out at 30° C. for 48 hours with stirring. After completion of the cultivation, the culture medium was centrifuged to collect the mycelium, which was then suspended in 200 ml of a buffer solution (pH 7.4) containing 15 mM tris-acetate, 25 mM sodium succinate and 2 mM magnesium acetate (hereinafter referred to as "Buffer solution B") to obtain a mycelial suspension of *Streptomyces roseosporus* A-5797. This suspension was again centrifuged to collect the mycelium, which was then suspended in 200 ml of Buffer solution B with thorough stirring. Forty ml of the suspension was placed in each of five 500 ml Erlenmeyer flasks and kept warm at 30° C. for 5 minutes. A solution of 200 µg of the substrate 25-hydroxyvitamin $D_3$ in 100 µl of ethanol was added to each of the five Erlenmeyer flasks, and the reaction was carried out at 30° C. for 90 minutes with shaking. The reaction mixtures were combined, and extracted with 1 l of methylene chloride. The methylene chloride layer was concentrated to dryness at 40° C. or below under reduced pressure, immediately dissolved in 7.5 ml of a mixture of 2-propanol and n-hexane (1:9) and allowed to stand at −20° C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm $\phi \times 25$ cm, Du Pont Co., U.S.A.) under the following conditions.

Eluent: 2-propanol:n-hexane = 1:9
Column temperature: 25° C.
Elution rate: 1.5 ml/minute
Detection: Use of Photodiode array detector (MCP 3500, Otsuka Electric Co.)

After elution, the peak fractions having a retention time of about 15.4 minutes and the same UV absorption pattern as those of the vitamin D compounds were collected, concentrated at 40° C. or below under reduced pressure, and applied to a high performance liquid chromatograph (Zorbax ODS, column size 4.6 mm $\phi \times 25$ cm, Du Pont Co., U.S.A.) under the following conditions.

Eluent: water:methanol = 1:9
Column temperature: 40° C.
Elution rate: 1.0 ml/minute
Detection: Use of Photodiode array detector (MCPD 3500, Otsuka Electric Co.)

After elution, the peak fractions having a retention time of about 5.6 minutes and the same UV absorption pattern as those of the vitamin D compounds were collected and concentrated to dryness at 40° C. or below under reduced pressure with a nitrogen gas replacement to give 200 µg of 1α, 25-dihydroxyvitamin $D_3$, which was identical to the authentic sample of the commercially available 1α, 25-dihydroxyvitamin $D_3$ (Duphar Co., Netherland) in terms of the retention time on a high performance liquid chromatograph (Zorbax SIL, column size 4.6 mm $\phi \times 25$ cm), the UV absorption spectrum and mass spectrum cleavage pattern.

Maximum UV Absorption: $\lambda_{max} = 265$ nm (ethanol).

EI-MS (m/z): 416(M+), 398(M+-H$_2$O), 380(M+-2H$_2$O), 287, 269, 258, 251, 152, 134, 129, 116, 111, 59.

EXAMPLE 7

Fifty ml of a sterile liquid medium (pH 7.0) containing 1.5% of glucose, 1.5% of soybean meal, 0.5% of corn steep liquor, 0.5% of sodium chloride and 0.2% of calcium carbonate, in each of five 500 ml Erlenmeyer flasks, was inoculated with one platinum loop of *Nocardia autotrophica* N-102, and shaking culture was carried out at 30° C. for 48 hours with stirring. After completion of the cultivation, the culture medium was centrifuged to collect the mycelium, which was then suspended in 200 ml of Buffer solution B to obtain mycelial suspension of *Nocardia autotrophica* N-102. This suspension was again centrifuged to collect the mycelium, which was then suspended in 200 ml of Buffer solution B with thorough stirring. Forty ml of the suspension was placed in each of five 500 ml Erlenmeyer flasks and kept warm at 30° C. for 5 minutes. A solution of 200 μg of the substrate 25-hydroxyvitamin D$_3$ in 100 μl of ethanol was added to each of the five Erlenmeyer flasks, and the reaction was carried out at 30° C. for 45 minutes with shaking. The reaction mixtures of the Erlenmeyer flasks were combined, and extracted with 1 l of methylene chloride. The methylene chloride layer was concentrated to dryness at 40° C. or below under reduced pressure, immediately dissolved in 7.5 ml of a mixture of 2-propanol and n-hexane (1:9) and allowed to stand at −20° C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm φ×25 cm, Du Pont Co., U.S.A.) under the following conditions.

Eluent: 2-propanol:n-hexane=1:9
Column temperature: 25° C.
Elution rate: 1.5 ml/minute
Detection: Use of Photodiode array detector (MCPD 3500, Otsuka Electric Co.)

After elution, the peak fractions having a retention time of about 15.4 minutes and the same UV absorption pattern as those of the vitamin D compounds were collected, concentrated at 40° C. or below under reduced pressure and applied to a high performance liquid chromatograph (Zorbax ODS, column size 4.6 mm φ×25 cm, Du Pont Co., U.S.A.) under the following conditions.

Eluent: water:methanol=1:9
Column temperature: 40° C.
Elution rate: 1.0 ml/minute
Detection: Use of Photodiode array detector (MCPD 3500, Otsuka Electric Co.)

After elution, the peak fractions having a retention time of about 5.6 minutes and the same UV absorption pattern as those of the vitamin D compounds were collected and concentrated to dryness at 40° C. or below under reduced pressure with a nitrogen gas replacement to give 100 μg of 1α, 25-dihydroxyvitamin D$_3$, which was identical to the authentic sample of the commercially available 1α, 25-dihydroxyvitamin D$_3$ (Duphar Co., Netherland) in terms of the retention time on a high performance liquid chromatograph (Zorbax SIL, column size 4.6 mm φ×25 cm), the UV absorption spectrum and mass spectrum cleavage pattern.

Maximum UV Absorption: λ$_{max}$=265 nm (ethanol).

EI-MS (m/z): 416(M+), 398(M+-H$_2$O), 380(M+-2H$_2$O), 287, 269, 258, 251, 152, 134, 129, 116, 111, 59.

EXAMPLE 8

Fifty ml of a sterile liquid medium (pH 7.0) containing 1% of starch, 1% of maltose, 1% of dextrin, 1.5% of soybean meal, 0.3% of meat extract, 0.5% of casamino acid and 0.4% of calcium carbonate, in each of five 500 ml Erlenmeyer flasks, was inoculated with one platinum loop of *Streptomyces sclerotialus* T-JS1, and shaking culture was carried out at 30° C. for 48 hours with stirring. After completion of the cultivation, the culture medium was centrifuged to collect the mycelium, which was then suspended in 200 ml of Buffer solution A. This mycelial suspension was again centrifuged to collect the mycelium, which was then suspended in 200 ml of Buffer solution A with thorough stirring. Forty ml of the suspension was placed in each of five 500 ml Erlenmeyer flasks and kept warm to 30° C. for 5 minutes. A solution of 200 g of the substrate 1α-hydroxyvitamin D$_3$ in 100 μl of ethanol was added to each of the five Erlenmeyer flasks, and the reaction was carried out at 30° C. for 90 minutes with stirring. The reaction mixtures were combined, and extracted with 1 l of methylene chloride. The methylene chloride layer was concentrated to dryness at 40° C. or below under reduced pressure, immediately dissolved in 7.5 ml of a mixture of 2-propanol and n-hexane (1:9) and allowed to stand at −20° C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm φ×25 cm, Du Pont Co., U.S.A.) under the following conditions.

Eluent: 2-propanol:n-hexane=1:9
Column temperature: 25° C.
Elution rate: 1.5 ml/minute
Detection: Use of Photodiode array detector (MCPD 3500, Otsuka Electric Co.)

After elution, the peak fractions having a retention time of about 15.4 minutes and the same UV absorption pattern as those of the vitamin D compounds were collected, concentrated at 40° C. or below under reduced pressure and applied to a high performance liquid chromatograph (Zorbax ODS, column size 4.6 mm φ×25 cm, Du Pont Co., U.S.A.) under the following conditions.

Eluent: water:methanol=1:9
Column temperature: 40° C.
Elution rate: 1.0 ml/minute
Detection: Use of Photodiode array detector (MCPD 3500, Otsuka Electric Co.)

After elution, the peak fractions having a retention time of about 5.6 minutes and the same UV absorption pattern as those of the vitamin D compounds were collected and concentrated to dryness at 40° C. or below under reduced pressure with a nitrogen gas replacement to give 20 μg of 1α, 25-dihydroxyvitamin D$_3$, which was identical to the authentic sample of the commercially available 1α, 25-dihydroxyvitamin D$_3$ (Duphar Co., Netherland) in terms of the retention time in a high performance liquid chromatograph (Zorbax SIL, column size 4.6 mm φ×25 cm), the UV absorption spectrum and mass spectrum cleavage pattern.

Maximum UV Absorption: λ$_{max}$=265 nm (ethanol).

EI-MS (m/z): 416(M+), 398(M+-H$_2$O), 380(M+-2H$_2$O), 287, 269, 251, 152, 134, 129, 116, 111, 59.

EXAMPLE 9

Fifty ml of a sterile liquid medium (pH 7.0) containing 1.5% of glucose, 1.5% of soybean meal, 0.5% of corn steep liquor, 0.5% of sodium chloride and 0.2% of calcium carbonate, in each of five 500 ml Erlenmeyer flasks, was inoculated with one platinum loop of *Streptomyces roseosporus* A-5797, and shaking culture was carried out at 30° C. for 48 hours with stirring. After completion of the cultivation, the culture medium was centrifuged to collect the mycelium, which was then suspended in 200 ml of Buffer solution B to obtain a mycelial suspension of *Streptomyces roseosporus* A-5797. This mycelial suspension was again centrifuged to collect the mycelium, which was then suspended in 200 ml of Buffer solution B with thorough stirring. Forty ml of the suspension was placed in each of five 500 ml Erlenmeyer flasks and kept warm at 30° C. for 5 minutes. A solution of 200 μg of the substrate 1α-hydroxyvitamin $D_3$ in 100 μl of ethanol was added to each of the five Erlenmeyer flasks, and the reaction was carried out at 30° C. for 180 minutes with shaking. The reaction mixtures of the Erlenmeyer flasks were combined, and extracted with 1 l of methylene chloride. The methylene chloride layer was concentrated to dryness at 40° C. or below under reduced pressure, immediately dissolved in 7.5 ml of a mixture of 2-propanol and n-hexane (1:9) and allowed to stand at −20° C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm φ×25 cm, Du Pont Co., U.S.A.) under the following conditions.

Eluent: 2-propanol:n-hexane=1:9
Column temperature: 25° C.
Elution rate: 1.5 ml/minute
Detection: Use of Photodiode array detector (MCPD 3500, Otsuka Electric Co.)

After elution, the peak fractions having a retention time of about 15.4 minutes and the same UV absorption pattern as those of the vitamin D compounds were collected, concentrated at 40° C. or below under reduced pressure and applied to a high performance liquid chromatograph (Zorbax ODS, column size 4.6 mm φ×25 cm, Du Pont Co., U.S.A.) under the following conditions.

Eluent: water:methanol=1:9
Column temperature: 40° C.
Elution rate: 1.0 ml/minute
Detection: Use of Photodiode array detector (MCPD 3500, Otsuka Electric Co.)

After elution, the peak fractions having a retention time of about 5.6 minutes and the same UV absorption pattern as those of the vitamn D compounds were collected and concentrated to dryness at 40° C. or below under reduced pressure with a nitrogen gas replacement to give 50 g of 1α, 25-dihydroxyvitamin $D_3$, which was identical to the authentic sample of the commercially available 1α, 25-dihydroxyvitamin $D_3$ (Duphar Co., Netherland) in terms of the retention time of a high performance liquid chromatograph (Zorbax SIL, column size 4.6 mm φ×25 cm), the UV absorption spectrum and mass spectrum cleavage pattern.

Maximum UV Absorption: $\lambda_{max}$=265 nm (ethanol).
EI-MS (m/z): 416(M+), 398(M+-$H_2O$), 380(M+-2$H_2O$), 287, 269, 251, 152, 134, 129, 116, 111, 59.

EXAMPLE 10

Fifty ml of a sterile liquid medium (pH 7.0) containing 1.5% of glucose, 1.5% of soybean meal, 0.5% of corn steep liquor, 0.5% of sodium chloride and 0.2% of calcium carbonate, in each of five 500 ml Erlenmeyer flasks, was inoculated with one platinum loop of *Nocardia autotrophica* N-102, and shaking culture was carried out at 30° C. for 48 hours with stirring. After completion of the cultivation, the culture medium was centrifuged to collect the mycelium, which was then suspended in 200 ml of Buffer solution B to obtain a mycelial suspension of *Nocardia autotrophica* N-102. This mycelial suspension was again centrifuged to collect the mycelium, which was then suspended in 200 ml of Buffer solution B with thorough stirring. Forty ml of the suspension was placed in each of five 500 ml Erlenmeyer flasks and kept warm at 30° C. for 5 minutes. A solution of 200 μg of the substrate 1α-hydroxyvitamin $D_3$ in 100 μl of ethanol was added to each of the five Erlenmeyer flasks, and the reaction was carried out at 30° C. for 90 minutes with stirring. The reaction mixtures of the Erlenmeyer flasks were combined, and extracted with 1 l of methylene chloride. The methylene chloride layer was concentrated to dryness at 40° C. or below under reduced pressure, immediately dissolved in 7.5 ml of a mixture of 2-propanol and n-hexane (1:9) and allowed to stand at −20° C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm φ×25 cm, Du Pont Co., U.S.A.) under the following conditions.

Eluent: 2-propanol:n-hexane=1:9
Column temperature: 25° C.
Elution rate: 1.5 ml/minute
Detection: Use of Photodiode array detector (MCPD 3500, Otsuka Electric Co.)

After elution, the peak fractions having a retention time of about 15.4 minutes and the same UV absorption pattern as those of the vitamin D compounds were collected, concentrated at 40° C. or below under reduced pressure and applied to a high performance liquid chromatograph (Zorbax ODS, column size 4.6 mm φ×25 cm, Du Pont Co., U.S.A.) under the following conditions.

Eluent: water:methanol=1:9
Column temperature: 40° C.
Elution rate: 1.0 ml/minute
Detection: Use of Photodiode array detector (MCPD 3500, Otsuka Electric Co.)

After elution, the peak fractions having a retention time of about 5.6 minutes and the same UV absorption pattern as those of the vitamin D compounds were collected and concentrated to dryness at 40° C. or below under reduced pressure with a nitrogen gas replacement to give 350 μg of 1α, 25-dihydroxyvitamin $D_3$, which was identical to the authentic sample of the commercially available 1α, 25-dihydroxyvitamin $D_3$ (Duphar Co., Netherland) in terms of the retention time at a high performance liquid chromatograph (Zorbax SIL, column size 4.6 mm φ×25 cm), the UV absorption spectrum and mass spectrum cleavage pattern.

Maximum UV Absorption: $\lambda_{max}$=265 nm (ethanol).
EI-MS (m/z): 416(M+), 398(M+-$H_2O$), 380(M+-2$H_2O$), 287, 269, 251, 152, 134, 129, 116, 111, 59.

EXAMPLE 11

Following a procedure similar to that of Example 8, 1α, 24, 25-trihydroxyvitamin $D_3$ was obtained from 1α, 24-dihydroxyvitamin $D_3$.

This compound had a retention time of 29.4 minutes in the high performance liquid chromatograph under the same conditions as those of Example 1.

Maximum UV Absorption: $\lambda_{max}=265$ nm (ethanol).

EI-MS (m/z): 432(M+), 414(M+-H$_2$O), 396(M+-2H$_2$O), 287, 269, 251, 152, 134, 129, 116, 59.

EXAMPLE 12

Fifty ml of a sterile liquid medium (pH 7.0) containing 1.5% of glucose, 1.5% of soybean meal, 0.5% of corn steep liquor, 0.5% of sodium chloride and 0.2% of calcium carbonate, in a 500 ml Erlenmeyer flask, was inoculated with one platinum loop of *Nocardia autotrophica* N-102, and shaking culture was carried out at 30° C. for 48 hours. To the culture medium of *Nocardia autotrophica* N-102 in logarithmic growth phase were added a solution of 5 mg of the substrate vitamin $D_3$ in 250 μl of ethanol and 0.5 ml of Tween-80, and then the mixture was subjected to shaking culture at 30° C. for 48 hours. After completion of the reaction, the culture medium was extracted with 200 ml of methylene chloride. The methylene chloride layer was concentrated to dryness at 40° C. or below under reduced pressure, immediately dissolved in 3 ml of a mixture of 2-propanol and n-hexane (1:9) and allowed to stand at −20° C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm φ×25 cm, Du Pont Co., U.S.A.) under the following conditions.

Eluent: 2-propanol:n-hexane=3:22
Column temperature: 25° C.
Elution rate: 1.5 ml/minute
Detection: Use of Photodiode array detector (Waters M990, Japan Millipore Co.)

After elution, the peak fractions having a retention time of about 4.0 minutes and the same UV absorption pattern as those of the vitamin D compounds were collected, concentrated at 40° C. or below under reduced pressure and applied to a high performance liquid chromatograph (Zorbax ODS, column size 4.6 mm φ×25 cm, Du Pont Co., U.S.A.) under the following conditions.

Eluent: water:methanol=1:9
Column temperature: 40° C.
Elution rate: 1.0 ml/minute
Detection: Use of Photodiode array detector (Waters M990, Japan Millipore Co.)

After elution, the peak fractions having a retention time of about 8.0 minutes and the same UV absorption pattern as those of the vitamin D compounds were collected and concentrated to dryness at 40° C. or below under reduced pressure with a nitrogen gas replacement to give 500 μg of 25-hydroxyvitamin $D_3$, which was identical to the authentic sample of the commercially available 25-hydroxyvitamin $D_3$ (Duphar Co., Netherland) in terms of the retention time in a high performance liquid chromatograph (Zorbax SIL, column size 4.6 mm φ×25 cm), the UV absorption spectrum and mass spectrum cleavage pattern.

Maximum UV Absorption: $\lambda_{max}=265$ nm (ethanol).

EI-MS (m/z): 400(M+), 382(M+-H$_2$O), 271, 253, 136, 118, 59.

EXAMPLE 13

Fifty ml of a sterilized liquid medium (pH 7.0) containing 1.5% of glucose, 1.5% of soybean meal, 0.5% of corn steep liquor, 0.5% of sodium chloride and 0.2% of calcium carbonate and 0.05% of magnesium sulfate in a 500 ml Erlenmeyer flask, was inoculated with one platinum loop of *Nocardia autotrophica* N-102, and shaking culture was carried out at 30° C. for 48 hours with stirring. To the culture medium of *Nocardia autotrophica* N-102 in logarithmic growth phase were added a solution of 5 mg of the substrate vitamin $D_3$ in 250 μl of ethanol and 0.05 ml of Tween-80, and then the mixture was subjected to shaking culture at 30° C. for 60 hours with stirring. After completion of the reaction, the culture medium was extracted with 200 ml of methylene chloride. The methylene chloride layer was concentrated to dryness at 40° C. or below under reduced pressure, immediately dissolved in 3 ml of a mixture of 2-propanol and n-hexane (1:9) and allowed to stand at −20° C. for 3 hours. The solution was centrifuged to remove the insoluble fractions, and the resulting supernatant was concentrated at 40° C. or below under reduced pressure and applied to a high performance liquid chromatograph (Zorbax SIL, column size 4.6 mm φ×25 cm, Du Pont Co., U.S.A.) under the following conditions.

Eluent: 2-propanol:n-hexane=3:22
Column temperature: 25° C.
Elution rate: 1.5 ml/minute
Detection: Use of Photodiode array detector (Waters M990, Japan Millipore Co.)

After elution, the peak fractions having a retention time of about 14.5 minutes and the same UV absorption pattern as those of the vitamin D compounds were collected, concentrated at 40° C. or below under reduced pressure and applied to a high performance liquid chromatograph (Zorbax ODS, column size 4.6 mm φ×25 cm, Du Pont Co., U.S.A.) under the following conditions.

Eluent: water:methanol=1:9
Column temperature: 40° C.
Elution rate: 1.0 ml/minute
Detection: Use of Photodiode array detector (Waters M990, Japan Millipore Co.)

After elution, the peak fractions having a retention time of about 5.6 minutes and the same UV absorption pattern as those of the vitamin D compounds were collected and concentrated to dryness at 40° C. or below under reduced pressure with a nitrogen gas replacement to give 50 μg of 1α, 25-dihydroxyvitamin $D_3$, which was identical to the authentic sample of the commercially available 1α, 25-dihydroxyvitamin $D_3$ (Duphar Co., Netherland) in terms of the retention time in a high performance liquid chromatograph (Zorbax SIL, column size 4.6 mm φ×25 cm), the UV absorption spectrum and mass spectrum cleavage pattern.

Maximum UV Absorption: $\lambda_{max}=265$ nm (ethanol).

EI-MS (m/z): 416(M+), 398(M+-H$_2$O), 380(M+-2H$_2$O), 287, 269, 251, 152, 134, 129, 116, 111, 59.

EXAMPLE 14

Following a procedure similar to that of Example 12, 25-hydroxyvitamin $D_2$ was obtained from vitamin $D_2$.

This compound had a retention time of 3.9 minutes in the high performance liquid chromatograph (Zorbax SIL, column size 4.6 mm $\phi \times 25$ cm) under the same conditions as those of Example 12.

Maximum UV Absorption: $\lambda_{max} = 265$ nm (ethanol).

EI-MS (m/z): 412(M+), 394(M+-H$_2$O), 271, 253, 136, 118, 59.

EXAMPLE 15

Following a procedure similar to that of Example 13, 1α, 25-dihydroxyvitamin D$_2$ was obtained from vitamin D$_2$.

This compound had a retention time of 13.8 minutes in the high performance liquid chromatograph (Zorbax SIL, column size 4.6 mm $\phi \times 25$ cm) under the same conditions as those of Example 13.

Maximum UV Absorption: $\lambda_{max} = 265$ nm (ethanol).

EI-MS (m/z): 428(M+), 410(M+-H$_2$O), 392(M+-2H$_2$O), 287, 269, 251, 152, 134, 116, 59.

EXAMPLE 16

(1) Fifty ml of a sterilized liquid medium (pH 7.0) containing 1.5% of glucose, 1.5% of soybean meal, 0.5% of corn steep liquor, 0.5% of sodium chloride and 0.2% of calcium carbonate in a 500 ml Erlenmeyer flask was inoculated with one platinum loop of *Nocardia autotrophica* N-102, and shaking culture was carried out at 28° C. for 96 hours with stirring.

(2) The following procedure was carried out at 2 to 8° C. The mycelium obtained in item (1) was suspended in 200 ml of a buffer solution (pH 7.4) containing 10 mM tris-acetate, 2 mM magnesium acetate, 7 mM 2-mercaptoethanol and 20% of glycerol (hereinafter referred to as "Buffer solution C"). The resulting mycelial suspension was centrifuged to give the mycelium, which was again suspended in 100 ml of Buffer solution C. This suspension was treated with a dispersor (ULTRA-TURRAX®: trade name, IKA-WERK CO.) for 2 minutes, and there was obtained the sonicated mycelium, which was then centrifuged to give a supernatant. Polyethylene glycol 6000 was added dropwise to the resulting supernatant to the final concentration of 25% with stirring, and the resulting solution was allowed to stand at 4° C. for 30 minutes. Then, the solution was centrifuged to remove the supernatant, and there was obtained the crude enzyme precipitate.

(3) The crude enzyme precipitate obtained in item (2) was added in an amount corresponding to 500 mg of protein to a solution (pH 7.4) containing 20 mM trisacetic acid, 70 mM nicotinamide, 2 mM magnesium acetate, 100 mM NADP, 5 mM ATP and 6 mM glucose-phosphoric acid. To 15 ml of the resulting enzyme reaction solution were added 5 units of glucose-phosphate dehydrogenase and a solution of 3 mg of vitamin D$_3$ in 150 µl of ethanol, and the mixture was shaken at 28° C. for 30 minutes for enzyme reaction.

(4) To the enzyme reaction solution obtained in item (3) were added 45 ml of a mixture of chloroform and methanol (1:2) so as to stop the enzyme reaction, and then the reaction product was extracted according to the method of Bligh and Deyer. After extraction, the resulting chloroform layer was concentrated to dryness at 40° C. or below under reduced pressure, immediately dissolved in 250 ml of 2-propanol and n-hexane (1:9), and the solution was applied to a high performance liquid chromatograph (Zorbax SIL, column size 4.6 mm $\phi \times 25$ cm, Du Pont Co., U.S.A.) under the following conditions.

Eluent: 2-propanol:n-hexane = 3:22
Column temperature: 25° C.
Elution rate: 1.5 ml/minute
Detection: Use of Photodiode array detector (MCPD 3500, Otsuka Electric Co.)

(5) After elution by the high performance liquid chromatograph in item (4), the peak fractions having a retention time of about 4.0 minutes and the same UV absorption pattern as those of the vitamin D compounds were collected, concentrated at 40° C. or below under reduced pressure and applied to a high performance liquid chromatograph (Zorbax ODS, column size 4.6 mm $\phi \times 25$ cm, Du Pont Co., U.S.A.) under the following conditions.

Eluent: water:methanol = 1:9
Column temperature: 40° C.
Elution rate: 1.0 ml/minute
Detection: Use of Photodiode array detector (MCPD 3500, Otsuka Electric Co.)

After elution, the peak fractions having a retention time of about 8.0 minutes and the same UV absorption pattern as those of the vitamin D compounds were collected and concentrated to dryness at 40° C. or below under reduced pressure with a nitrogen gas replacement to give 166 µg of 25-hydroxyvitamin D$_3$, which was identical to the authentic sample of the commercially available 25-hydroxyvitamin D$_3$ (Duphar Co., Netherland) in terms of the retention time in a high performance liquid chromatograph (Zorbax SIL, column size 4.6 mm $\phi \times 25$ cm, the UV absorption spectrum and mass spectrum cleavage pattern.

Maximum UV Absorption: $\lambda_{max} = 265$ nm (ethanol).

EI-MS (m/z): 400(M+), 382(M+-H$_2$O), 271, 253, 136, 118, 59.

(6) After elution in the high performance liquid chromatograph in item (4), the peak fractions having a retention time of about 14.5 minutes and the same UV absorption pattern as those of the vitamin D compounds were collected, concentrated at 40° C. or below under reduced pressure and applied to a high performance liquid chromatograph (Zorbax ODS, column size 4.6 mm $\phi \times 25$ cm, Du Pont Co., U.S.A.) under the following conditions.

Eluent: water:methanol = 1:9
Column temperature: 40° C.
Elution rate: 1.0 ml/minute
Detection: Use of Photodiode array detector (MCPD 3500, Otsuka Electric Co.)

After elution, the peak fractions having a retention time of about 8.0 minutes and the same UV absorption pattern as those of the vitamin D compounds were collected and concentrated to dryness at 40° C. or below under reduced pressure with a nitrogen gas replacement to give 20 µg of 25-hydroxyvitamin D$_3$, which was identical to the authentic sample of the commercially available 1α, 25-hydroxyvitamin D$_3$ (Duphar Co., Netherland) in terms of the retention time in a high performance liquid chromatograph (Zorbax SIL, column size 4.6 mm $\phi \times 25$ cm, the UV absorption spectrum and mass spectrum cleavage pattern.

Maximum UV Absorption: $\lambda_{max} = 265$ nm (ethanol).

EI-MS (m/z): 416(M+), 398(M+-H$_2$O), 380(M+-2H$_2$O), 287, 238, 241, 152, 134, 129, 116, 111, 59.

Experiment

In vitro radioreceptor assay method of 1α, 25-dihydroxyvitamin D$_3$

1α, 25-Dihydroxyvitamin D$_3$ receptor prepared from fetal chicken intestine (Yamasa Shoyu Co.) was suspended in a buffer solution (pH 7.4) containing 10 mM tris-acetate, 0.5 mM EDTA, 1 mM dithiothreitol and 10 mM sodium molybdate to give a receptor solution (protein: about 0.5 mg/1).

To the suspension was added each 3 μl and 10 μl of the test drug [the authentic sample of 1α, 25-dihydroxyvitamin $D_3$ (Duphar Co., Netherland)] and the 1α, 25-dihydroxyvitamin $D_3$ compound obtained in Example 1 dissolved in 50% ethanol, respectively, to give $10^{-9}$ –$10^{-5}$ M concentration. $^3$H-1α, 25-Dihydroxyvitamin $D_3$ (about 4 μM) was then added, and incubation was carried out at 0° C. for 3 hours. Separation of receptor binding substance and no-binding substance was carried out according to the charcoal method. The specific binding amount is calculated by subtracting non-specific binding amount obtained in the presence of 10 μM 1α, 25-dihydroxyvitamin $D_3$ from the total binding amount obtained in the above reaction. The binding ability of the test drug is expressed as a concentration ($IC_{50}$) of 50% inhibition of the binding to receptor with 1α, 25-dihydroxyvitamin $D_3$.

| Test drug: 1α, 25-dihydroxyvitamin $D_3$ | $IC_{50}$ (nM) |
| --- | --- |
| Authentic sample | 32 |
| Compound obtained in Example 1 | 32 |
| Compound obtained in Example 6 | 32 |
| Compound obtained in Example 7 | 32 |
| Compound obtained in Example 8 | 32 |
| Compound obtained in Example 13 | 32 |
| Compound obtained in Example 16 | 32 |

As indicated above, the activities of 1α, 25-dihydroxyvitamin $D_3$'s obtained in Examples 1, 6, 7, 8, 13 and 16 are identical to those of the commercially available authentic sample in the test of in vitro radioreceptor assay method.

What is claimed is:

1. A method for preparing a 1α- or 25-hydroxyvitamin D compound which comprises adding a vitamin D compound having a hydrogen atom at the 1α- or 25-position to a reaction mixture containing a mycelium of Actinomycetales being capable of hydroxylating the vitamin D compound or to a reaction mixture containing the enzyme produced from said mycelium and converting the hydrogen atom into a hydroxyl group.

2. A method for preparing a 25-hydroxyvitamin D compound or 1α, 25-dihydroxyvitamin D compound which comprises adding a vitamin D compound having hydrogen atoms at the 1α- and 25-positions to a reaction mixture containing a mycelium of Actinomycetales being capable of hydroxylating the vitamin D compound or to a reaction mixture containing enzyme produced from said mycelium and converting the hydrogen atoms into hydroxyl groups.

3. A method according to claim 1 wherein the Actinomycetales is genus Streptomyces or Nocardia.

4. A method according to claim 2 wherein the Actinomycetales is Streptomyces or Nocardia.

5. A method according to claim 1 wherein the Actinomycetales is *Streptomyces sclerotialus* T-JS1.

6. A method according to claim 2 wherein the Actinomycetales is *Streptomyces sclerotialus* T-JS1.

7. A method according to claim 1 wherein the Actinomycetales is *Streptomyces roseosporus* A-5797.

8. A method according to claim 2 wherein the Actinomycetales is *Streptomyces roseosporus* A-5797.

9. A method according to claim 1 wherein the Actinomycetales is *Nocardia autotrophica* N-102.

10. A method according to claim 2 wherein the Actinomycetales is *Nocardia autotrophica* N-102.

* * * * *

UNITED STATES PATENT AND TRADEMARK OFFICE
CERTIFICATE OF CORRECTION

PATENT NO. : 4,892,821

DATED : January 9, 1990

INVENTOR(S) : OMURA et al

It is certified that error appears in the above-identified patent and that said Letters Patent is hereby corrected as shown below:

Col. 2, line 4, "1αor" should read --1α- or;

line 47, "prefecture" should read --Prefecture--;

line 51, "BP-1370,," should read --BP-1370,--; and line 62, after "and" insert --which--.

Col. 4, line 38, after "observed" insert a period --.--.

Col. 5, line 27, "Pridham/Godlieb" should read --(Pridham/Godlieb--; and line 31, after "lizable" insert a colon --:--.

Col. 6, line 46, "Pridham/Godlieb" should read --(Pridham/Godlieb--.

Col. 8, line 50, "processed" should read --proceeded--.

Col. 14, line 63, "at" should read --in--.

Col. 15, line 11, delete "129,".

Col. 17, line 47, "trisa" should read --tris-a--.

Col. 18, line 28, between "cm" and "," insert a close parenthesis --)--;

line 48, "8.0" should read --5.6--;

line 52, before "25-" insert --1α, --;

line 52, "hydroxyvitamin" should read --dihydroxyvitamin--;

UNITED STATES PATENT AND TRADEMARK OFFICE
CERTIFICATE OF CORRECTION

PATENT NO. : 4,892,821

DATED : January 9, 1990

INVENTOR(S) : OMURA et al

It is certified that error appears in the above-identified patent and that said Letters Patent is hereby corrected as shown below:

Col. 18, line 54, before "25-" insert --1α,--;

line 54, "hydroxyvitamin" should read --dihydroxyvitamin--; and line 60, delete "238, 241" and insert --269, 251--.

Col. 20, line 8, delete "the".

Signed and Sealed this

Twelfth Day of February, 1991

Attest:

HARRY F. MANBECK, JR.

Attesting Officer — Commissioner of Patents and Trademarks